(12) United States Patent
Furukawa et al.

(10) Patent No.: US 6,448,428 B1
(45) Date of Patent: Sep. 10, 2002

(54) FLUORINE-CONTAINING ORGANIC SILICON COMPOUND AND METHOD FOR ITS PRODUCTION

(75) Inventors: Yutaka Furukawa; Takashige Yoneda, both of Kanagawa (JP)

(73) Assignee: Asahi Glass Company, Limited, Tokyo (JP)

( * ) Notice: Subject to any disclaimer, the term of this patent is extended or adjusted under 35 U.S.C. 154(b) by 0 days.

(21) Appl. No.: 10/002,140

(22) Filed: Dec. 5, 2001

Related U.S. Application Data

(63) Continuation of application No. PCT/JP01/02779, filed on Mar. 30, 2001.

(30) Foreign Application Priority Data

Apr. 7, 2000 (JP) ........................................ 2000-106835

(51) Int. Cl.$^7$ .................................................. C07F 7/08
(52) U.S. Cl. ...................... 556/448; 556/445; 556/447; 556/463; 106/12; 106/13; 106/287.12
(58) Field of Search ................................ 556/445, 447, 556/448, 463, 12, 13, 287.12

(56) References Cited

U.S. PATENT DOCUMENTS

| | | | |
|---|---|---|---|
| 3,681,418 A | * 8/1972 | Pierce et al. | 556/463 |
| 3,794,736 A | 2/1974 | Abbott et al. | |
| 5,041,588 A | * 8/1991 | Caporiccio | 556/463 |
| 5,834,612 A | 11/1998 | Furukawa et al. | |
| 5,834,614 A | 11/1998 | Furukawa et al. | |
| 6,197,989 B1 | 3/2001 | Furukawa et al. | |

FOREIGN PATENT DOCUMENTS

| | | |
|---|---|---|
| JP | 7-233026 | 9/1995 |
| JP | 11-116943 | 4/1999 |

* cited by examiner

*Primary Examiner*—Paul F. Shaver
(74) *Attorney, Agent, or Firm*—Oblon, Spivak, McClelland, Maier & Neustadt, P.C.

(57) ABSTRACT

A fluorine-containing organic silicon compound represented by the following formula (1):

$$\qquad (1)$$

provided that the symbols in the formula (1) have the following meanings:

$R^1$ and $R^2$: respectively independently monovalent hydrocarbon groups;

$A^f$: a group represented by the following formula (2), (3), (4) or (5):

$$A^1-X^1- \qquad (2)$$

$$A^2-X^2-O-X^1- \qquad (3)$$

$$A^1-X^2-O-X^1- \qquad (4)$$

$$A^2-X^1- \qquad (5)$$

provided that the symbols in the formulae (2), (3), (4) and (5) have the following meanings:

$A^1$: a monovalent polyfluorohydrocarbon group;

$A^2$: a monovalent polyfluorohydrocarbon group containing an etheric oxygen atom;

$X^1$: $-(CH_2)_a-$ (a is an integer of at least 3);

$X^2$: a bivalent hydrocarbon group.

11 Claims, No Drawings

FLUORINE-CONTAINING ORGANIC SILICON COMPOUND AND METHOD FOR ITS PRODUCTION

This application is a continuation of International Application No. PCT/JP01/02779 filed on Mar. 30, 2001.

BACKGROUND OF THE INVENTION

Field of the Invention

The present invention relates to a novel fluorine-containing organic silicon compound and a method for its production. Particularly, it relates to a fluorine-containing organic silicon compound having a hydroxyl group directly bonded to a silicon atom, and a method for its production.

DESCRIPTION OF THE BACKGROUND

An organic silicon compound having fluorine atoms is excellent in e.g. lubricating properties, water and oil repellency and oil and chemical resistance and thus is applied to various industrial fields. For example, when it is used as an additive to a surface treating agent or a resin, it is possible to impart the above-mentioned properties to the surface of a substrate or a molded product of the resin. As a specific example of such a fluorine-containing organic silicon compound, a fluorine-containing silane coupling agent made of a compound represented by the following formula (11) may be mentioned.

$$ASiY_3 \tag{11}$$

(In the formula (11), A represents $R(CH_2)_2-$ (R is a perfluoroalkyl group), Y represents a hydrolysable group such as a halogen atom or an alkoxy group.)

Further, in a method of hydrolyzing a non-fluorine type silicon compound having a Si—Y moiety to produce a corresponding compound having a Si—OH moiety, a method of reacting while dropwise adding ammonia to the reaction system, is known.

However, in a case where the surface of a substrate was treated with a fluorine-containing silane coupling agent made of a compound represented by the formula (11), there was a problem that attached water remained on the surface, although the surface showed water and oil repellency and oil and chemical resistance.

Further, in the method of reacting while dropwise adding ammonia, the reaction operation was cumbersome, and it was necessary to control the flow rate in order to maintain the pH in the reaction system within a predetermined range. Further, use of ammonia brought about a problem from the viewpoint of working environment or a problem of odor.

SUMMARY OF THE INVENTION

The present invention has an object to provide a novel fluorine-containing organic silicon compound excellent in e.g. lubricating properties, water and oil repellency, and oil and chemical resistance. Namely, it has an object to provide a fluorine-containing organic silicon compound useful as an additive to be added to a surface treating agent and various resin compositions. A surface treating agent containing the compound as an essential component, is capable of imparting to the surface of a substrate a nature of readily removing water attached to the surface of the substrate.

DETAILED DESCRIPTION OF THE PREFERRED EMBODIMENTS

The present invention provides a fluorine-containing organic silicon compound represented by the following formula (1):

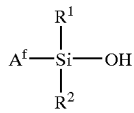
(1)

provided that the symbols in the formula (1) have the following meanings:

$R^1$ and $R^2$: respectively independently monovalent hydrocarbon groups;

$A^f$: a group represented by the following formula (2), (3), (4) or (5):

$$A^1-X^1- \tag{2}$$

$$A^2-X^2-O-X^1- \tag{3}$$

$$A^1-X^2-O-X^1- \tag{4}$$

$$A^2-X^1- \tag{5}$$

provided that the symbols in the formulae (2), (3), (4) and (5) have the following meanings:

$A^1$: a monovalent polyfluorohydrocarbon group;

$A^2$: a monovalent polyfluorohydrocarbon group containing an etheric oxygen atom;

$X^1$: $-(CH_2)_a-$ (a is an integer of at least 3);

$X^2$: a bivalent hydrocarbon group. Further, the present invention provides a method for producing a fluorine-containing silicon compound represented by the above formula (1), which comprises hydrolyzing a fluorine-containing silicon compound represented by the following formula (10). Namely, it provides a method for producing a fluorine-containing organic silicon compound, wherein the hydrolysis is carried out while neutralizing hydrogen halide formed during the hydrolysis with a base.

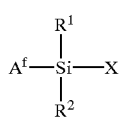
(10)

provided that the symbols in the formula (10) have the following meanings:

X: a halogen atom;

$R^1$, $R^2$ and $A^f$: the same meanings as the meanings in the formula (1).

The fluorine-containing organic silicon compound of the present invention is represented by the following formula (1):

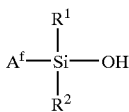

(1)

In the following, the meanings of the symbols in the formula (1) will be explained.

In the present invention, "a hydrocarbon group" means a group comprising carbon atoms and hydrogen atoms unless otherwise specified. The hydrocarbon group may be an aromatic hydrocarbon group or an aliphatic hydrocarbon group, but it is preferably an aliphatic hydrocarbon group. As a monovalent aliphatic hydrocarbon group, an alkyl group is preferred. As a bivalent aliphatic hydrocarbon group, an alkylene group is preferred, and a polymethylene group is more preferred. The number of carbon atoms in an alkyl group and in an alkylene group is preferably from about 1 to 10, particularly preferably from 1 to 4. Further, the alkyl group and the alkylene group are preferably of a straight chain structure.

$R^1$ and $R^2$ respectively independently represent monovalent hydrocarbon groups, preferably methyl groups.

$A^f$ is a group represented by the following formula (2), (3), (4) or (5):

  (2)

  (3)

  (4)

  (5)

Here, $A^1$ represents a monovalent polyfluorohydrocarbon group. The "monovalent polyfluorohydrocarbon group" means a group having at least two hydrogen atoms of a monovalent hydrocarbon group substituted by fluorine atoms. As such a group, a polyfluoroalkyl group is preferred.

The number of fluorine atoms in the polyfluorohydrocarbon group is preferably at least 60%, more preferably at least 80%, when it is represented by (the number of fluorine atoms in the polyfluorohydrocarbon group)/(the number of hydrogen atoms in a hydrocarbon group having the same number of carbon atoms corresponding to the polyfluorohydrocarbon group)×100(%). Particularly preferred is a perfluorohydrocarbon group wherein it is substantially 100% (a group having substantially all of hydrogen atoms of a hydrocarbon group substituted by fluorine atoms).

The structure of the monovalent polyfluorohydrocarbon group may be a straight chain or branched structure, but a straight chain structure is preferred. In the case of a branched structure, the branched moiety is preferably a short chain having from about 1 to 3 carbon atoms, and it is preferably a structure wherein the branched moiety is present at a terminal portion of $A^1$.

$A^1$ is particularly preferably a perfluoroalkyl group.

The following examples may be mentioned as specific examples of $A^1$. Further, structurally isomeric groups other than the following are included in $A^1$.

$C_4F_9$— (including structural isomeric groups such as $CF_3(CF_2)_3$—, $(CF_3)_2CFCF_2$—, $(CF_3)_3C$— and $CF_3CF_2CF(CF_3)$—), $C_5F_{11}$— (including structural isomeric groups such as $CF_3(CF_2)_4$—, $(CF_3)_2CF(CF_2)_2$—, $(CF_3)_3CCF_2$— and $CF_3(CF_2)_2CF(CF_3)$—), $C_6F_{13}$— (including structural isomeric groups such as $CF_3(CF_2)_2C(CF_3)_2$—), $C_8F_{17}$—, $C_{10}F_{21}$—, $C_{12}F_{25}$—, $C_{14}F_{29}$—, $C_{16}F_{33}$—, $C_{18}F_{37}$—, $C_{20}F_{41}$— and $(CF_3)_2CF(CF_2)_s$— (s is an integer of 0 or at least 1).

$A^2$ represents a monovalent polyfluorohydrocarbon group containing an etheric oxygen atom. The "polyfluorohydrocarbon group containing an etheric oxygen atom" means a group having one or at least two etheric oxygen atoms inserted between a carbon-carbon bond of the above-mentioned polyfluorohydrocarbon group. As such a group, a group containing a polyfluorooxyalkylene moiety is preferred.

$A^2$ is particularly preferably a group containing perfluorooxyalkylene, more preferably a group containing perfluorooxyalkylene and having a perfluoroalkyl group at the terminal. As such a perfluorooxyalkylene, perfluorooxymethylene, perfluorooxyethylene, perfluorooxypropylene or perfluorooxybutylene may, for example, be mentioned.

Specific examples of $A^2$ may be $CF_3(CF_2)_4OCF(CF_3)$—, $F[CF(CF_3)CF_2O]_uCF(CF_3)CF_2CF_2$— (u is an integer of at least 1), $F[CF(CF_3)CF_2O]_rCF(CF_3)$— (r is an integer of at least 1), $F(CF_2CF_2CF_2O)_vCF_2CF_2$— (v is an integer of at least 1), $F(CF_2CF_2O)_wCF_2CF_2$— (w is an integer of at least 1), and $F[CF(CF_3)CF_2O]_z CF(CF_3)CF_2OCF_2CF_2$— (z is an integer of at least 1).

$X^1$ represents —$(CH_2)_a$— (a is an integer of at least 3). a is preferably an integer of from 3 to 6, particularly preferably 3 or 4.

$X^2$ is a bivalent hydrocarbon group. As such a group, an alkylene group is preferred. $X^2$ may have a straight chain or branched structure, and a straight chain structure is preferred. Particularly preferred is a straight chain alkylene group represented by —$(CH_2)_p$— (p is an integer of from 1 to 10). Especially preferred is a straight chain alkylene group wherein p is an integer of from 2 to 4. In the case of a branched structure, the branched moiety is preferably a short chain wherein the number of carbon atoms is from about 1 to 3.

In the fluorine-containing organic silicon compound of the present invention, the above formula (2) is preferably a group represented by the following formula (6).

  (6)

In the formula (6), n represents an integer of from 1 to 18. Preferably, n is an integer of from 4 to 12. $X^1$ is as defined above.

Specific examples of the group represented by the above formula (6) may be $C_4F_9$—$(CH_2)_3$—, $C_4F_9$—$(CH_2)_4$—, $C_5F_{11}$—$(CH_2)_3$—, $C_5F_{11}$—$(CH_2)_4$—, $C_6F_{13}$—$(CH_2)_3$—, $C_6F_{13}$—$(CH_2)_4$—, $C_7F_{15}$—$(CH_2)_3$—, $C_7F_{15}$—$(CH_2)_4$—, $C_8F_{17}$—$(CH_2)_3$—, $C_8F_{17}$—$(CH_2)_4$—, $C_9F_{19}$—$(CH_2)_3$—, $C_9F_{19}$—$(CH_2)_4$—, $C_{10}F_{21}$—$(CH_2)_3$— and $C_{10}F_{21}$—$(CH_2)_4$.

Further, as the perfluoroalkyl groups in the above specific examples, structurally isomeric groups may be mentioned, and a straight chain perfluoroalkyl group is preferred.

Further, in the fluorine-containing organic silicon compound of the present invention, the above formula (3) is preferably a group represented by the following formula (7):

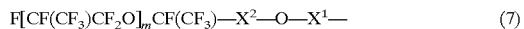  (7)

In the formula (7), m is an integer of from 1 to 10. m is preferably an integer of from 1 to 5. $X^1$ and $X^2$ are as defined above, and $X^2$ is preferably a straight chain alkylene group.

Specific examples of the group represented by the above formula (7) may be $F[CF(CF_3)CF_2O]_2CF(CF_3)CH_2O(CH_2)_3$—, and $F[CF(CF_3)CF_2O]CF(CF_3)CH_2O(CH_2)_3$—.

Further, in the fluorine-containing organic silicon compound of the present invention, the above formula (4) is preferably a group represented by the following formula (8):

$$C_kF_{2k+1}-X^2-O-X^1- \quad (8)$$

In the formula (8), k is an integer of from 1 to 18. k is preferably an integer of from 4 to 12. $X^1$ and $X^2$ are as defined above, and $X^2$ is preferably a straight chain alkylene group.

Specific examples of the group represented by the above formula (8) may be $C_4F_9-(CH_2)_2-O-(CH_2)_3-$, $C_6F_{13}-(CH_2)_2-O-(CH_2)_3-$, $C_8F_{17}-(CH_2)_3-O-(CH_2)_3-$ and $C_8F_{17}-(CH_2)_2-O-(CH_2)_3-$. Further, the above specific examples include structural isomeric groups.

Further, in the fluorine-containing organic silicon compound of the present invention, the above formula (5) is preferably a group represented by the following formula (9):

$$F[CF(CF_3)CF_2O]_vCF(CF_3)-CF_2OCF_2CF_2-X^1- \quad (9)$$

In the formula (9), v is an integer of at least 0. v is preferably an integer of from 1 to 3. $X^1$ is as defined above, preferably $-(CH_2)_3-$.

A specific example of the group represented by the above formula (9) may be $F[CF(CF_3)CF_2O]CF(CF_3)CF_2OCF_2CF_2-CH_2CH_2CH_2-$.

The following compounds may be mentioned as specific preferred examples of the fluorine-containing organic silicon compound of the present invention. Further, the following specific examples include structural isomeric groups.

$C_4F_9(CH_2)_3Si(CH_3)_2OH$, $C_8F_{17}(CH_2)_3Si(CH_3)_2OH$, $C_8F_{17}(CH_2)_4Si(CH_3)_2OH$, $C_{10}F_{21}(CH_2)_3Si(CH_3)_2OH$, $C_8F_{17}(CH_2)_2-O-(CH_2)_3Si(CH_3)_2OH$, $C_8F_{17}(CH_2)_3-O-(CH_2)_3Si(CH_3)_2OH$, $F[CF(CF_3)CF_2O]CF(CF_3)CH_2O(CH_2)_3Si(CH_3)_2OH$, $F[CF(CF_3)CF_2O]_2CF(CF_3)CH_2O(CH_2)_3Si(CH_3)_2OH$, $F[CF(CF_3)CF_2O]CF(CF_3)CF_2OCF_2CF_2(CH_2)_3Si(CH_3)_2OH$.

As a method for producing the fluorine-containing organic silicon compound of the present invention, a method of hydrolyzing a fluorine-containing organic silicon compound represented by the following formula (10) for the production, is preferred. Namely, it is preferred to carry out the hydrolysis while neutralizing hydrogen halide (HX) formed during the hydrolysis, with a base.

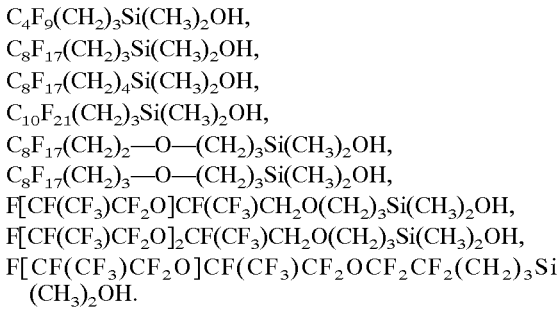

(10)

$$A^f-\underset{\underset{R^2}{|}}{\overset{\overset{R^1}{|}}{Si}}-X$$

In the formula (10), X represents a halogen atom. As X, a chlorine atom is preferred. $R^1$, $R^2$ and $A^f$ are as defined above.

Specific examples of the fluorine-containing organic silicon compound represented by the above formula (10) may be compounds having hydroxyl groups of the compounds described above as specific preferred examples of the fluorine-containing organic silicon compound of the present invention, substituted by chlorine atoms or bromine atoms. The method of obtaining the fluorine-containing organic silicon compound represented by the above formula (10) is not particularly limited. For example, it can be synthesized by a reaction (hereinafter referred to also as "hydrosililation") wherein a H—Si moiety of a compound represented by the following formula (16) is added to a fluorine-containing unsaturated compound represented by the following formula (12), (13), (14) or (15):

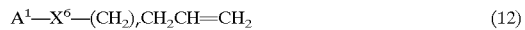
$$A^1-X^6-(CH_2)_r CH_2CH=CH_2 \quad (12)$$

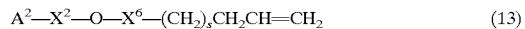
$$A^2-X^2-O-X^6-(CH_2)_s CH_2CH=CH_2 \quad (13)$$

$$A^1-X^2-O-X^6-(CH_2)_t CH_2CH=CH_2 \quad (14)$$

$$A^2-X^6-(CH_2)_r CH_2CH=CH_2 \quad (15)$$

In the formulae (12) to (15), each of r, s and t represents an integer of 0 or at least 1, preferably 0, 1 or 2, particularly preferably 0. $A^1$, $A^2$ and $x^2$ are as defined above. $X^6$ represents a single bond or a bivalent hydrocarbon group.

(16)

$$H-\underset{\underset{R^2}{|}}{\overset{\overset{R^1}{|}}{Si}}-X$$

In the formula (16), $R^1$, $R^2$ and X are as defined above.

Specific examples of the fluorine-containing unsaturated compound represented by the above formula (12) may be $C_4F_9CH_2CH=CH_2$, $C_8F_{17}CH_2CH=CH_2$, $C_8F_{17}(CH_2)_2CH=CH_2$ and $C_{10}F_{21}CH_2CH=CH_2$.

Specific examples of the fluorine-containing unsaturated compound represented by the above formula (13) may be $F[CF(CF_3)CF_2O]CF(CF_3)-CH_2-O-CH_2CH=CH_2$, and $F[CF(CF_3)CF_2O]_2CF(CF_3)-CH_2-O-CH_2CH=CH_2$.

Specific examples of the fluorine-containing unsaturated compound represented by the above formula (14) may be $C_8F_{17}(CH_2)_2-O-CH_2CH=CH_2$ and $C_8F_{17}(CH_2)_3-O-CH_2CH=CH_2$.

A specific example of the fluorine-containing unsaturated compound represented by the above formula (15) may be $F\{CF(CF_3)CF_2O\}CF(CF_3)-CF_2-O-CF_2CF_2CH_2CH=CH_2$.

In the hydrosililation, the amount of the fluorine-containing unsaturated compound represented by the above formulae (12) to (15) is preferably at least one equivalent, more preferably from 1.1 to 2 equivalents, per equivalent of hydrogen atoms bonded to the silicon atom in the compound represented by the above formula (16).

The hydrosililation is carried out preferably in the presence of a catalyst. As the catalyst, a catalyst containing a transition metal is preferred, and a catalyst containing at least one selected from platinum, rhodium and cobalt, is particularly preferred. The amount of the catalyst is usually from about 1 to 10 ppm in the reaction system. However, in the present invention, it is preferably from about 0.01 to 10 ppm, since the reaction proceeds in a short time even when the amount of the catalyst is small in the present invention.

The hydrosililation may be carried out in the presence of a solvent, or substantially in the absence of a solvent. It is preferably carried out in the absence of a solvent. In the absence of a solvent, the amount of a solvent contained in the reaction system is most preferably 0 (not contained at all). However, a solvent may be present in such an amount to be used for the preparation of a reagent to be used for the reaction. For example, a small amount of a solvent used for dissolving the catalyst may be present. The amount of a solvent in the reaction system is preferably at most 1 mass %, more preferably from 0 to 0.1 mass %. When the reaction is carried out substantially in the absence of a solvent, there is a merit in that no solvent will remain in the formed fluorine-containing organic silicon compound represented by the above formula (1), and a product of high quality can be obtained. Further, post treatment after the reaction can easily be carried out.

The reaction temperature is preferably from about 70 to 100° C. in a usual case.

The reaction time may be suitably changed depending upon the compound to be used. It is usually from about 0.5 to 10 hours. However, in the case of the present invention, it is preferably from 0.5 to 5 hours, particularly preferably from 3 to 5 hours, since the reaction proceeds even in a short period of time.

The fluorine-containing organic silicon compound of the present invention is preferably produced by a method of hydrolyzing the fluorine-containing organic silicon compound represented by the above formula (10) while neutralizing hydrogen halide formed during the hydrolysis, with a base.

As the base to be used for the production of the fluorine-containing organic silicon compound of the present invention, an inorganic base is preferred. Particularly preferred is an inorganic weak base such as calcium carbonate, sodium bicarbonate or magnesium carbonate. The amount of the base may be at least equivalent to the acid to be formed. The amount of the base is preferably from 1 to 1.5 equivalents, particularly preferably from 1 to 1.05 equivalents, to the amount of the acid to be formed.

Further, the amount of water to be used for the hydrolytic reaction, may be at least equivalent to X (halogen atoms) stoichiometrically. When an inorganic weak base is used as the base, it is preferably used as dispersed or suspended in water. In such a case, in order to have the inorganic weak base sufficiently dispersed or suspended, the concentration of the base is preferably from 1 to 30 mass %, particularly preferably from 5 to 15 mass %. The inorganic base dispersed or suspended in water, is preferably permitted to be present from the beginning of the reaction so that the reaction system may not be acidic.

Further, at the time of carrying out the hydrolytic reaction, a solvent of ether type may be employed. The reaction temperature is preferably at most 10° C.

If the above hydrolytic reaction is carried out without using a base, a compound represented by the following formula (17) which is a dehydrated condensate of a hydrolyzate (formula (1)) of the fluorine-containing organic silicon compound, will be formed in a large amount:

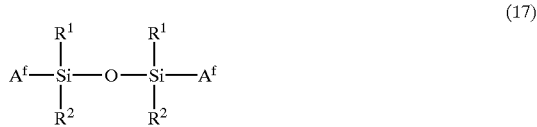

(17)

In the formula (17), $R^1$, $R^2$ and $A^f$ are as defined above.

Whereas, when the production method of the present invention is employed, the fluorine-containing organic silicon compound represented by the above formula (1), of high quality, can be produced without formation of the compound represented by the formula (17). Further, in a case where the inorganic base is used as dispersed or suspended in water, there is a merit that separation of the organic layer and the aqueous layer after the reaction can easily be carried out. If ammonia is used, the resulting salt serves as a kind of an emulsifier to form a suspension state, whereby separation tends to be difficult.

The fluorine-containing organic silicon compound of the present invention is excellent in e.g. lubrication properties, water and oil repellency, and oil and chemical resistance, and it has a nature to lower the surface tension or refractive index and is also excellent in e.g. electrical insulating properties, release properties, defoaming properties and heat resistance.

The fluorine-containing organic silicon compound of the present invention can be used as various functional materials required to have the above properties. For example, when it is applied as a surface treating agent for the treatment of a substrate, it is capable of imparting properties such as lubrication properties, water and oil repellency, and oil and chemical resistance to the surface of the substrate. Further, by its addition to a functional oil, a resin, rubber, etc., it is possible to lower the surface tension or refractive index or to impart e.g. electrical insulation properties, release properties, water repellency, defoaming properties, oil resistance, solvent resistance, lubrication properties or heat resistance. Particularly when it is used as a surface treating agent, treatment by coating is easy, and water attached to the surface can easily be removed.

Further, the fluorine-containing organic silicon compound of the present invention is a useful compound which can be used as an intermediate for various fluorine-containing organic silicon compounds.

The fluorine-containing organic silicon compound of the present invention has a reactive hydroxyl group at its terminal, whereby when it is used as a surface treating agent for the treatment of the surface of a substrate, it is possible to impart properties such as water and oil repellency, and oil and chemical resistance to the surface of the substrate. Further, by its addition to a resin, rubber, etc., it is possible to lower the surface tension or refractive index or to impart properties such as electrical insulating properties, release properties, water repellency, defoaming properties, oil resistance, solvent resistance, lubricating properties or heat resistance, to the resin, rubber, etc. Especially when it is used as a surface treating agent, it is possible to impart a property whereby water attached to the surface can easily be removed.

Further, as shown in the following Reference Examples, it is useful as a starting material for various industrial materials which are required to have properties such as water and oil repellency, stain-proofing properties and release properties.

EXAMPLES

The present invention will be described in detail with reference to Examples. The present invention is by no means restricted to such Examples.

Example 1

Into a glass container for reaction having a capacity of 0.5 l and equipped with a thermometer, a dropping funnel and a stirrer, water (150 g) and CaCO$_3$ (2.71 g) were put and stirred, and the internal temperature was maintained to be from 0 to 50° C. Then, a solution having F(CF$_2$)$_8$(CH$_2$)$_3$Si(CH$_3$)$_2$Cl (30 g) dissolved in diethyl ether (100 ml) was dropwise added from the dropping funnel, and while maintaining the internal temperature of the flask at a level of not higher than 5° C., stirring was continued for 30 minutes after completion of the dropwise addition.

The reaction was terminated upon confirming the disappearance of F(CF$_2$)$_8$(CH$_2$)$_3$Si(CH$_3$)$_2$Cl by gas chromatography. After the termination of the reaction, double layer separation was carried out, and the organic layer was dried by adding magnesium sulfate. After removing magnesium sulfate by filtration, diethyl ether was removed by an evaporator. $F(CF_2)_8(CH_2)_3Si(CH_3)_2OH$ (28.4 g) as a fluorine-containing organic silicon compound of the present invention was obtained as a white solid.

The NMR spectrum and the IR spectrum of the above compound are as follows.

$^1H$—NMR δ (ppm): 0.18 (Si—$CH_3$), 0.69 (Si—$CH_2$), 1.56 (Si—OH), 1.70 ($CH_2$—$\underline{CH_2}$—$CH_2$), 2.11 ($CF_2$—$CH_2$)

$^{19}F$—NMR δ (ppm): -81.7 ($CF_3$), -115.1 (—$CH_2CF_2$—) -122.5~-124.1 (—$CF_2$—), -126.9 (—$C\underline{F_2}CF_3$)

IR ($cm^{-1}$): 3680 (Si—OH), 1360~1300 (C—$F_3$) 1250~1050 (C—$F_2$), 1255 (Si—$CH_3$), 1100 (Si—O)

Reference Example 1

Into a glass container for reaction having a capacity of 0.2 l and equipped with a thermometer and a stirrer, [($CH_3$)$_2SiO$]$_3$ (13.8 g), $F(CF_2)_8(CH_2)_3Si(CH_3)_2OH$ (10) obtained in Example 1, and tetrahydrofuran (hereinafter referred to as THF, 60 ml) were put, and the internal temperature was maintained to be 20° C. Then, n-$C_4H_9Li$ (a 15% hexane solution, 45 μl) was put, followed by polymerization.

After confirming disappearance of [($CH_3$)$_2SiO$]$_3$ by gas chromatography, ($CH_3$)$_2HSiCl$ (1.85 g) was put, followed by stirring for one hour. After completion of the reaction, water (100 ml) was put, followed by double layer separation, whereupon the organic layer was washed with a 5% sodium hydrogen carbonate aqueous solution, followed by double layer separation again, whereupon the organic layer was dried by adding magnesium sulfate. After removing magnesium sulfate by filtration, a volatile component was removed under a condition of 100° C./50 mmHg (=100° C./6.667×10$^4$ Pa, the same applies hereinafter). A transparent oil (23.7 g) represented by the following structural formula, was obtained.

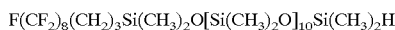

$F(CF_2)_8(CH_2)_3Si(CH_3)_2O[Si(CH_3)_2O]_{10}Si(CH_3)_2H$

The NMR spectrum and the IR spectrum of the above compound are as follows.

$^1H$—NMR δ (ppm): 0.18 (Si—$CH_3$), 0.69 (Si—$CH_2$), 1.70 ($CH_2$—$\underline{CH_2}$—$CH_2$), 2.11 ($CF_2$—$CH_2$), 4.72 (Si—H)

$^{19}F$—NMR δ (ppm): -81.7 ($CF_3$), -115.1 (—$CH_2CF_2$—), -122.5~-124.1 (—$CF_2$—), -126.9 (—$C\underline{F_2}CF_3$)

IR ($cm^{-1}$): 2150 (Si—H) 1360~1300 (C—$F_3$), 1250~1050 (C—$F_2$), 1255 (Si—$CH_3$), 1100 (Si—O)

Reference Example 2

Into a glass container for reaction having a capacity of 0.2 l and equipped with a thermometer and a stirrer, [$F(CF_2)_4(CH_2)_2Si(CH_3)O$]$_3$ (57.0 g), $F(CF_2)_8(CH_2)_3Si(CH_3)_2OH$ (10 g) obtained in Example 1, and THF (60 ml) were put, and the internal temperature was maintained to be 20° C. Then, n-$C_4H_9Li$ (a 15% hexane solution, 45 μl) was put, followed by polymerization.

After confirming disappearance of [$F(CF_2)_4(CH_2)_2Si(CH_3)O$]$_3$ by gas chromatography, ($CH_3$)$_2HSiCl$ (1.85 g) was put, followed by stirring for one hour. After completion of the reaction, water (100 ml) was put, followed by double layer separation. The organic layer was washed with a 5% sodium hydrogen carbonate aqueous solution, followed by double layer separation again, whereupon the organic layer was dried by an addition of magnesium sulfate. After removing magnesium sulfate by filtration, a volatile component was removed under a condition of 100° C./50 mmHg. A transparent oil (64.7 g) represented by the following structural formula, was obtained.

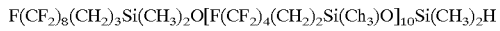

$F(CF_2)_8(CH_2)_3Si(CH_3)_2O[F(CF_2)_4(CH_2)_2Si(Ch_3)O]_{10}Si(CH_3)_2H$

The NMR spectrum and the IR spectrum of the above compound are as follows.

$^1H$—NMR δ (ppm): 0.18 (Si—$CH_3$), 0.69 (Si—$CH_2$), 1.70 ($CH_2$—$\underline{CH_2}$—$CH_2$), 2.11 ($CF_2$—$CH_2$), 4.72 (Si—H)

$^{19}F$—NMR δ (ppm): -81.7 ($CF_3$) -115.1 (—$CH_2CF_2$—), -122.5~-124.1 (—$CF_2$—), -126.9 (—$C\underline{F_2}CF_3$)

IR ($cm^{-1}$): 2150 (Si—H), 1360~1300 (C—$F_3$), 1250~1050 (C—$F_2$), 1255 (Si—$CH_3$), 1100 (Si—O)

Reference Example 3

Into a glass container for reaction having a capacity of 0.1 l and equipped with a thermometer and a stirrer, the oil (27.4 g) obtained in Reference Example 2, $CH_2$=$CHSi(OCH_3)_3$ (1.12 g) and a 10% isopropanol solution of chloroplatinic acid (0.1 g) were put, and then, the temperature was raised to 90° C., followed by stirring for one hour.

The reaction was terminated upon confirming disappearance of the peak of H—Si by IR. After termination of the reaction, a volatile component was removed under a condition of 100° C./50 mmHg. A transparent oil (27.9 g) represented by the following structural formula, was obtained.

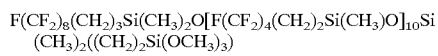

$F(CF_2)_8(CH_2)_3Si(CH_3)_2O[F(CF_2)_4(CH_2)_2Si(CH_3)O]_{10}Si(CH_3)_2((CH_2)_2Si(OCH_3)_3)$

The NMR spectrum and the IR spectrum of the above compound are as follows.

$^1H$—NMR δ (ppm): 0.18 (Si—$CH_3$), 0.69 (Si—$CH_2$), 1.70 ($CH_2$—$\underline{CH_2}$—$CH_2$), 2.11 ($CF_2$—$CH_2$), 3.68 (Si—$OCH_3$)

$^{19}F$—NMR δ (ppm): -81.7 ($CF_3$), -115.1 (—$CH_2CF_2$—) -122.5~-124.1 (—$CF_2$—), -126.9 (—$C\underline{F_2}CF_3$)

IR ($cm^{-1}$): 1360~1300 (C—$F_3$), 1250~1050 (C—$F_2$), 1255 (Si—$CH_3$), 1100 (Si—O)

Reference Example 4

Into a glass container for reaction having a capacity of 0.2 l and equipped with a thermometer and a stirrer, [($CH_3$)$_2SiO$]$_3$ (13.8 g), $F(CF_2)_8(CH_2)_3Si(CH_3)_2OH$ (10 g) obtained in Example 1, and tetrahydrofuran (THF, 60 ml) were put, and the internal temperature was maintained to be 20° C. Then, n-$C_4H_9Li$ (a 15% hexane solution, 34 μl) was put, followed by polymerization.

After confirming disappearance of [($CH_3$)$_2SiO$]$_3$ by gas chromatography, $Si(OCH_3)_4$ (4.25 g) was put, followed by stirring for one hour. After completion of the reaction, a volatile component was removed under a condition of 100° C./50 mmHg, and then, pressure filtration was carried out. A transparent oil (24.8 g) represented by the following structural formula, was obtained.

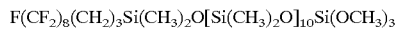

$F(CF_2)_8(CH_2)_3Si(CH_3)_2O[Si(CH_3)_2O]_{10}Si(OCH_3)_3$

The NMR spectrum and the IR spectrum of the above compound are as follows.

$^1H$—NMR δ (ppm): 0.18 (Si—$CH_3$), 0.69 (Si—$CH_2$), 1.70 ($CH_2$—$\underline{CH_2}$—$CH_2$), 2.11 ($CF_2$—$CH_2$), 3.80 (Si—$OCH_3$)

$^{19}F$—NMR δ (ppm): -81.7 ($CF_3$), -115.1 (—$CH_2CF_2$—), -122.5~-124.1 (—$CF_2$—), -126.9 (—$C\underline{F_2}CF_3$)

IR ($cm^{-1}$): 2150 (Si—H), 1360~1300 (C—$F_3$), 1250~1050 (C—$F_2$), 1255 (Si—$CH_3$), 1100 (Si—O)

Example 2

Application of the Fluorine-Containing Organic Silicon Compound of the Present Invention $F(CF_2)_8(CH_2)_3Si(CH_3)_2OH$ obtained in Example 1, was dissolved at a concentration of 3 mass % in an isopropanol solution. Glass was immersed in this solution for 30 seconds and then immersed in isopropanol, thereby to remove excess $F(CF_2)_8(CH_2)_3Si(CH_3)_2OH$. This glass was baked at 200° C. for 3 minutes, whereupon the contact angle was 110°, thus indicating that the glass surface was provided with water repellency. Then, a water droplet of 50 μl was placed on this glass disposed horizontally, and the glass was gradually inclined, whereby the water droplet moved at an angle of 5°.

Comparative Example 1

A glass surface was treated in the same manner as in Example 2, by using $F(CF_2)_8(CH_2)_3Si(OCH_3)_3$ instead of $F(CF_2)_8(CH_2)_3Si(CH_3)_2OH$. The contact angle was 110°, thus indicating that the glass surface was provided with water repellency. Then, a water droplet of 50 μl was placed on this glass disposed horizontally, and the glass was gradually inclined, whereby the water droplet moved at an angle of 30°.

The entire disclosure of Japanese Patent Application No. 2000-106835 filed on Apr. 7, 2000 including specification, claims, drawings and summary are incorporated herein by reference in its entirety.

What is claimed is:

1. A fluorine-containing organic silicon compound represented by the following formula (1):

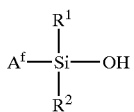
(1)

provided that the symbols in the formula (1) have the following meanings:

$R^1$ and $R^2$: respectively independently monovalent hydrocarbon groups;

$A^f$: a group represented by the following formula (2), (3), (4) or (5):

$A^1—X^1—$ (2)

$A^2—X^2—O—X^1—$ (3)

$A^1—X^2—O—X^1—$ (4)

$A^2—X^1—$ (5)

provided that the symbols in the formulae (2), (3), (4) and (5) have the following meanings:

$A^1$: a monovalent polyfluorohydrocarbon group;

$A^2$: a monovalent polyfluorohydrocarbon group containing an etheric oxygen atom;

$X^1$: $—(CH_2)_a—$ (a is an integer of at least 3);

$X^2$: a bivalent hydrocarbon group.

2. The fluorine-containing organic silicon compound according to claim 1, which satisfies any one of the conditions that the formula (2) is a group represented by the following formula (6), the formula (3) is a group represented by the following formula (7), the formula (4) is a group represented by the following formula (8), and the formula (5) is a group represented by the following formula (9):

$C_nF_{2n+1}—X^1—$ (6)

$F[CF(CF_3)CF_2O]_nCF(CF_3)—X^2—O—X^1—$ (7)

$C_kF_{2k+1}—X^2—O—X^1—$ (8)

$F[CF(CF_3)CF_2O]_kCF(CF_3)—CF_2OCF_2CF_2—X^1—$ (9)

provided that the symbols in the formulae (6), (7), (8) and (9) have the following meanings:

n: an integer of from 1 to 18;
m: an integer of from 1 to 10;
k: an integer of from 1 to 18;
v: an integer of at least 0;
$X^1$ and $X^2$: the same meanings as in the formula (2), (3), (4) or (5).

3. The fluorine-containing organic silicon compound according to claim 1, wherein $X^2$ is represented by $—(CH_2)_p—$ (p is an integer of from 1 to 10).

4. A method for producing a fluorine-containing organic silicon compound represented by the above formula (1), which comprises hydrolyzing a fluorine-containing organic silicon compound represented by the following formula (10), wherein the hydrolysis is carried out while neutralizing hydrogen halide formed during the hydrolysis with a base:

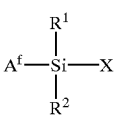
(10)

provided that the symbols in the formula (10) have the following meanings:

X: a halogen atom;
$R^1$, $R^2$ and $A^f$: the same meanings as the meanings in the formula (1).

5. The method for producing a fluorine-containing silicon compound according to claim 4, wherein the base is an inorganic base dispersed or suspended in water.

6. The method for producing a fluorine-containing silicon compound according to claim 5, wherein the hydrolysis is carried out in the presence of the inorganic base dispersed or suspended in water, in the reaction system, from the beginning of the reaction.

7. A surface treating agent comprising a fluorine-containing organic silicon compound as defined in claim 1, as an essential component.

8. The fluorine-containing organic silicon compound according to claim 1, wherein $A^1$ is a perfluoroalkyl group.

9. The fluorine-containing organic silicon compound according to claim 1, wherein $A_2$ is a group comprising perfluorooxyalkylene.

10. The fluorine-containing organic silicon compound according to claim 3, wherein p is an integer of from 2 to 4.

11. The fluorine-containing organic silicon compound according to claim 1, which comprises:

$C_4F_9(CH_2)_3Si(CH_3)_2OH$,
$C_8H_{17}(CF_2)_3Si(CH_3)_2OH$,
$C_8H_{17}(CH_2)_4Si(CH_3)_2OH$,
$C_{10}F_{21}(CH_2)_3Si(CH_3)_2OH$,
$C_8F_{17}(CH_2)_2—O—(CH_2)_3Si(CH_3)_2OH$,
$C_8F_{17}(CH_2)_3—O—(CH_2)_3Si(CH_3)_2OH$,
$F(CF(CF_3)CF_2O)CF(CF_3)CH_2O(CH_2)_3Si(CH_3)_2OH$,
$F(CF(CF_3)CF_2O)_2CF(CF_3)CH_2O(CH_2)_3Si(CH_3)_2OH$, or
$F(CF(CF_3)CF_2O)CF(CF_3)CF_2OCF_2CF_2(CH_2)_3Si(CH_3)_2OH$, or structural isomers thereof.

* * * * *